United States Patent [19]
Adair

[11] Patent Number: 5,251,613
[45] Date of Patent: Oct. 12, 1993

[54] METHOD OF CERVICAL VIDEOSCOPE WITH DETACHABLE CAMERA

[76] Inventor: Edwin L. Adair, 2800 S. University Blvd., Denver, Colo. 80210

[21] Appl. No.: 895,731

[22] Filed: Jun. 9, 1992

Related U.S. Application Data

[62] Division of Ser. No. 695,727, May 6, 1991, Pat. No. 5,143,054.

[51] Int. Cl.$^5$ .............................................. A61B 1/06
[52] U.S. Cl. .......................................... 128/6; 128/18
[58] Field of Search ............... 128/6, 17, 18, 395–398; 606/13–16; 604/263; 354/62; 358/98

[56] References Cited

U.S. PATENT DOCUMENTS

| | | | |
|---|---|---|---|
| 3,789,835 | 2/1974 | Whitman | 128/18 |
| 4,522,196 | 6/1985 | Cunningham et al. | 128/6 |
| 4,590,923 | 5/1986 | Watanabe | 128/6 |
| 4,597,383 | 7/1986 | VanDerBel | 128/18 |
| 4,878,485 | 11/1989 | Adair | 128/6 |
| 4,914,521 | 4/1990 | Adair | 128/6 |

*Primary Examiner*—Max Hindenburg
*Attorney, Agent, or Firm*—Fields, Lewis, Pittenger & Rost

[57] ABSTRACT

A simple yet highly useful cervical videoscope has been provided which can easily be used by the doctor to examine the cervix and vagina for cancerous lesions or other abnormalities. Also, because of the small size of the video camera unit there is sufficient space between the video camera unit and the blades of the speculum for inserting forceps and other instruments that may need to be used. By using the cervical videoscope in combination with a monochromator the physician can step the wavelength of light from one end of the light spectrum to the other until he observes florescence which identifies abnormal cells. Thereupon, he can destroy the cells by use of a laser beam. When he observes that no more florescence,is occurring, then he can discontinue the operation of the laser, knowing that the lesion has been completely eradicated. Also, a channel for drawing a suction to remove smoke created by the destruction of the lesion can be provided. The video camera unit also is adjustable along a guide on the fixed blade of the speculum to focus it. The video camera unit can be removed from the speculum and inserted into a sterile sheath for reinsertion into the vagina for examination for lesions and areas covered by the speculum blade. It can also be inserted into the colon and other body passageways where lesions are suspected. The video camera unit can be removed from the sheath, resterilized or disinfected and reattached to a sterile speculum for use with another patient.

4 Claims, 3 Drawing Sheets

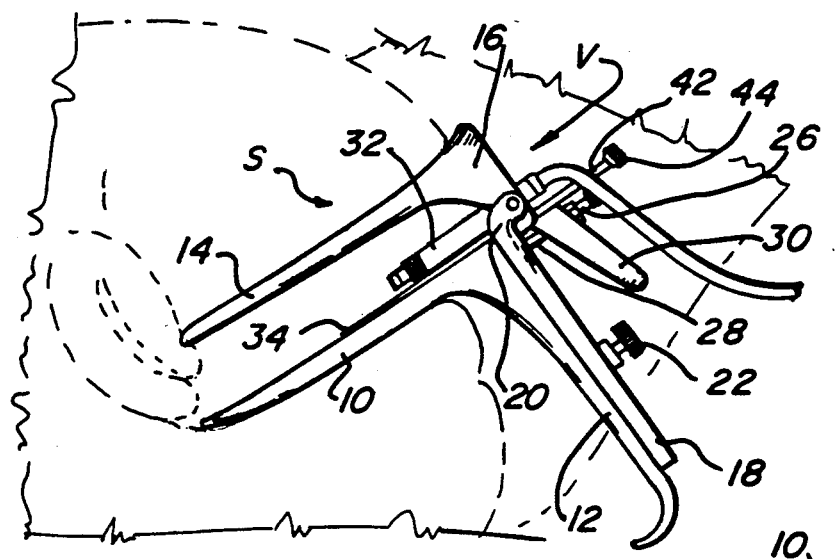
Fig_1
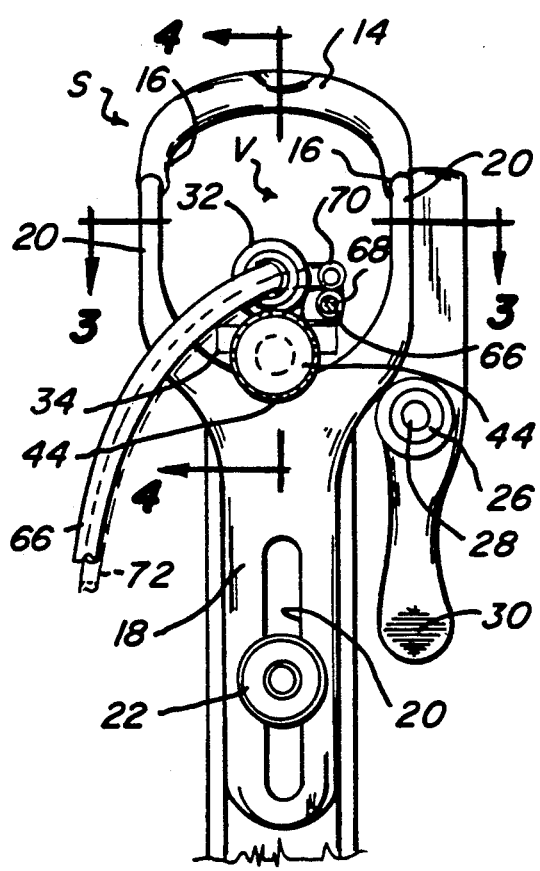
Fig_2
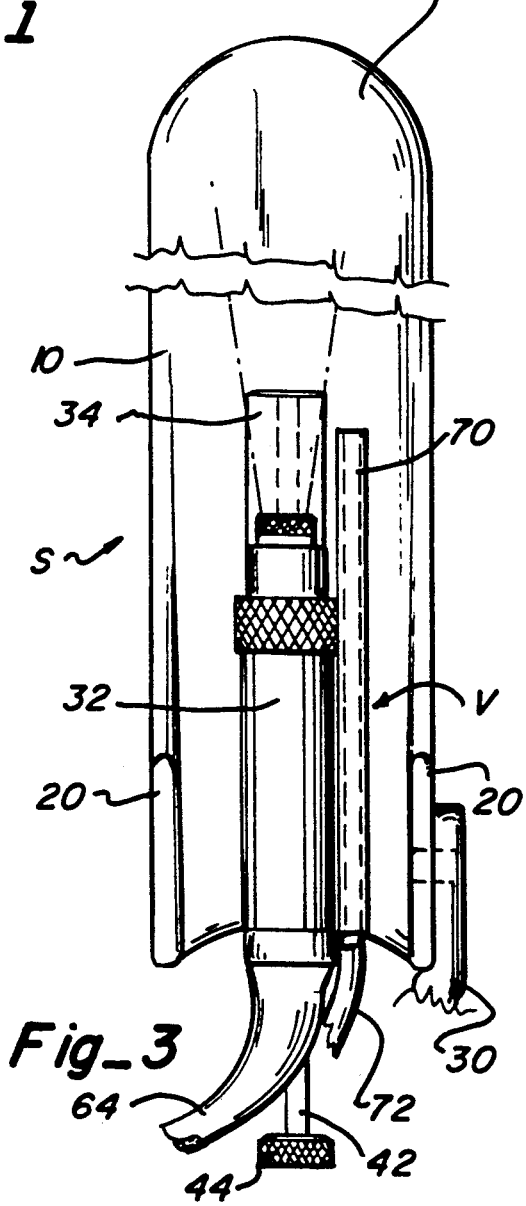
Fig_3

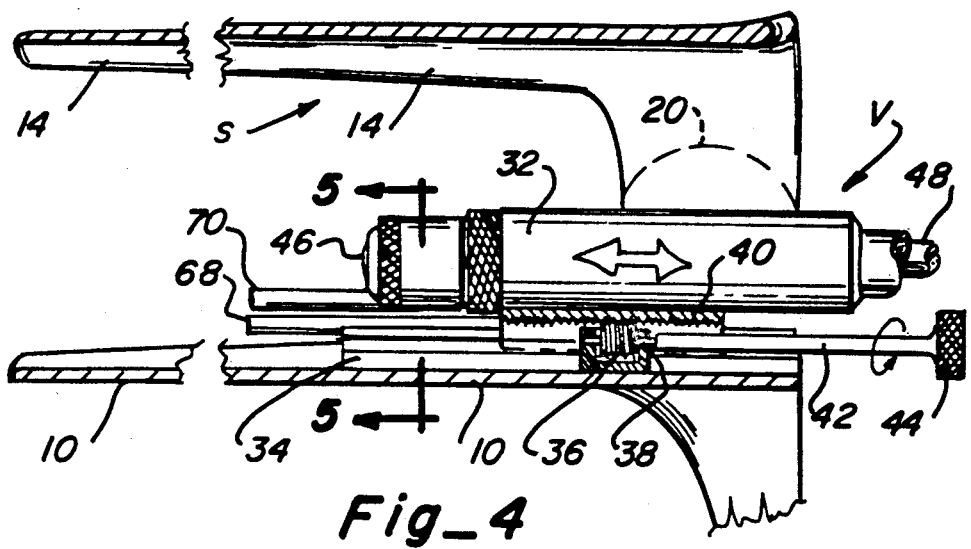
Fig_4
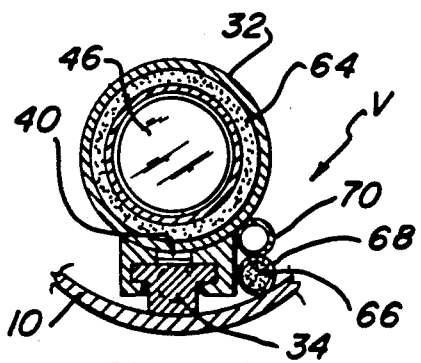
Fig_5
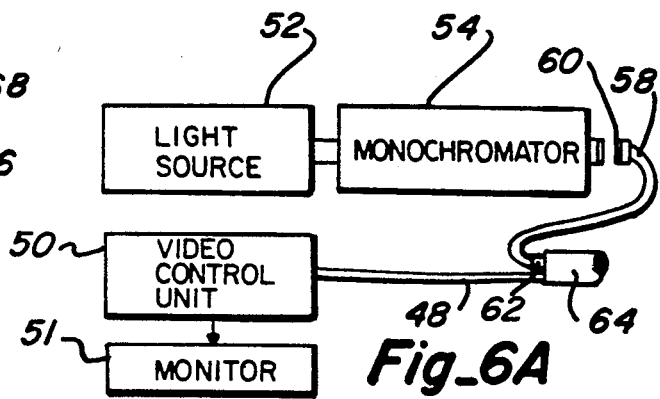
Fig_6A
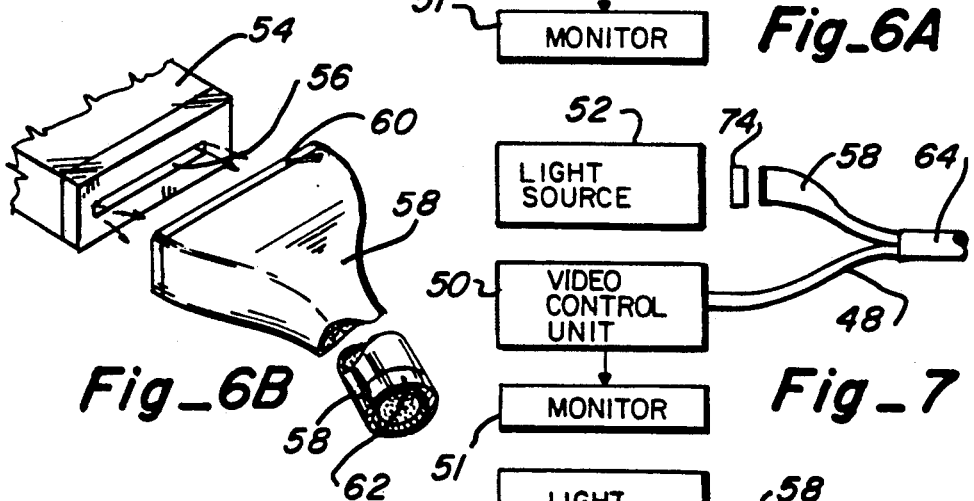
Fig_6B
Fig_7
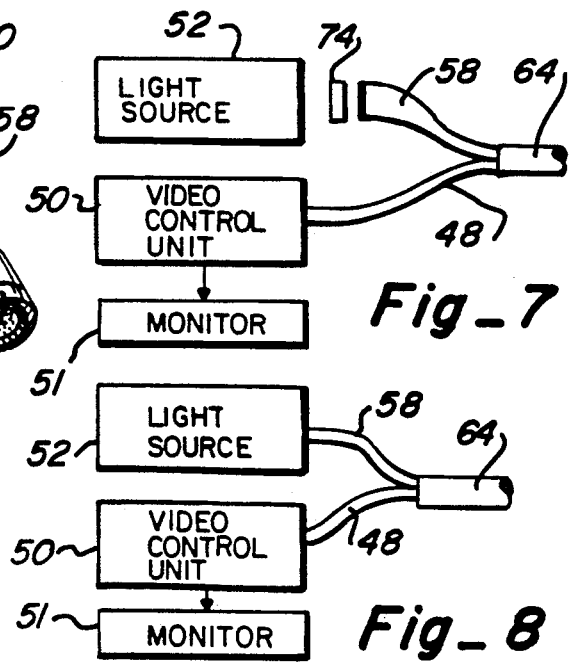
Fig_8

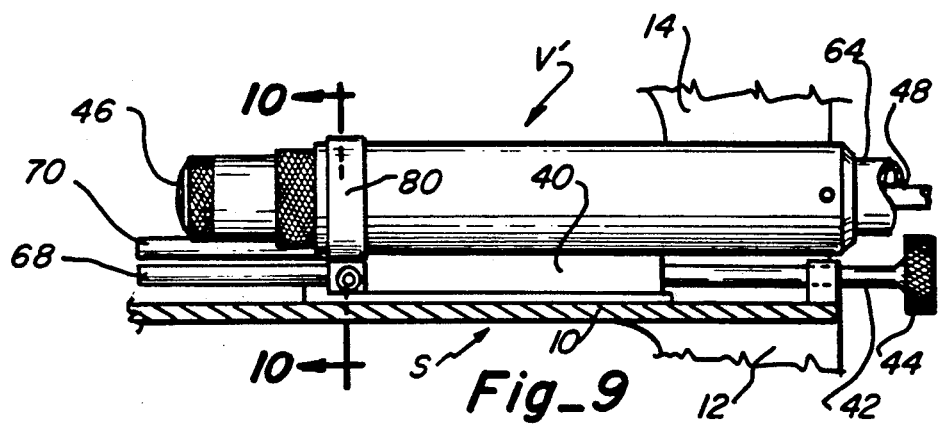
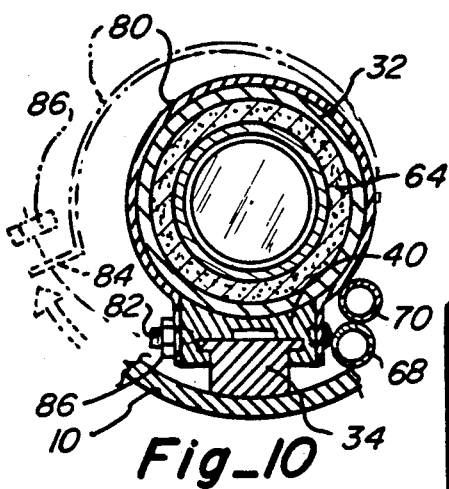
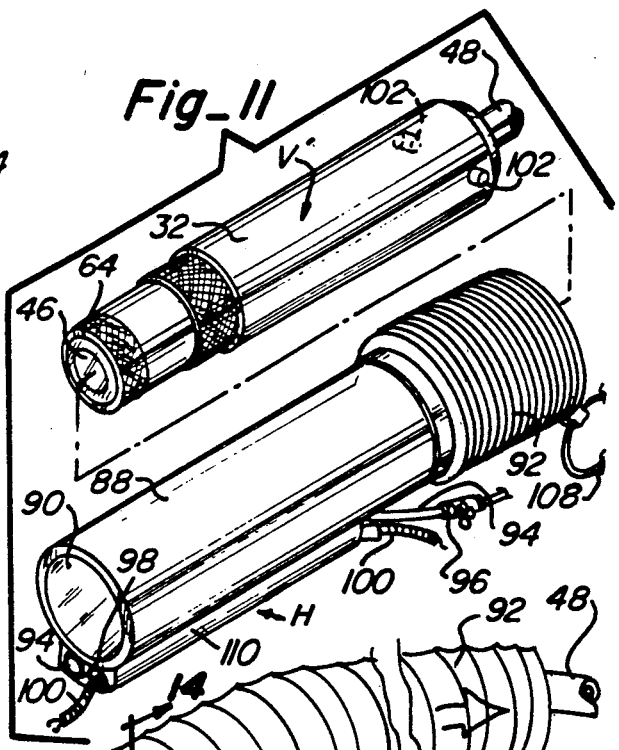
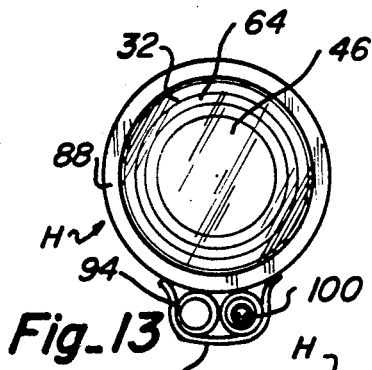
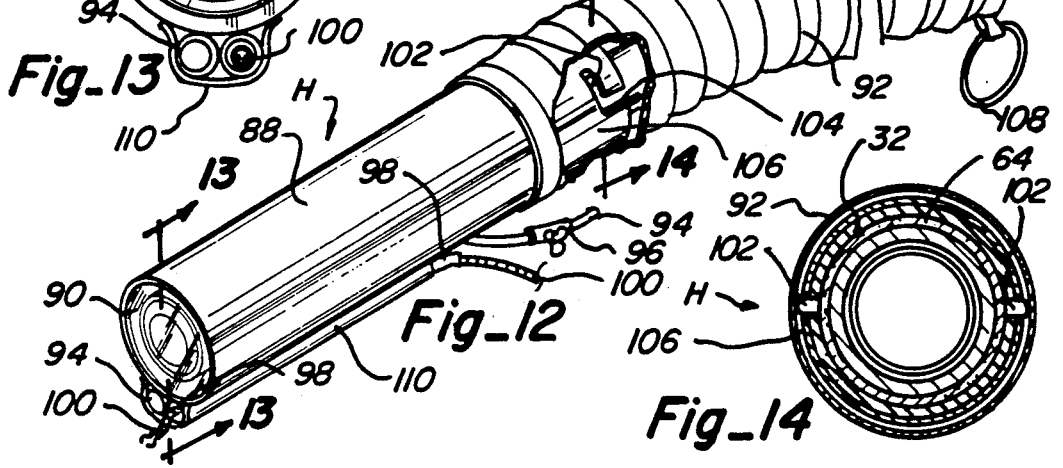

METHOD OF CERVICAL VIDEOSCOPE WITH DETACHABLE CAMERA

This application is a division of U.S. Ser. No. 695,727, filed May 6, 1991, now U.S. Pat. No. 5,143,054.

TECHNICAL FIELD

This invention relates to a cervical videoscope and particularly to one with a removable camera unit which allows inspection of the cervix and other body passageways under specific selected wavelength of light and provides for subsequent treatment of any lesions found. The camera unit includes a camera, optics and light delivery system, which may also be referred to as an electronic video endoscope.

BACKGROUND ART

Examination of the cervix for cancer and viral infections are done now with a device called a colposcope. This device is a binocular microscope which is placed near the patient. It supplies a bright light, (white light and green light) and the operator looks through the eyepieces of the colposcope much like looking through field glasses. This is done with a vaginal speculum in place. Some of the devices have camera attachments for still picture photography. The physician looks at the tissue looking for whitened areas after treatment with 3-54 acetic acid. The acetic acid whitens tissue which is low in raucous, such as cancer cells. The physician also looks for clusters of blood vessels which may indicate new growth such as cancer. The effectiveness of this colposcopy procedure is only 85%, and this is with a very experienced physician doing the procedure. Also, the colposcope is difficult to use because of its size and weight.

Over the years various vaginal speculae have been developed. Among these are the following:

Casaneda U.S. Pat. No. 4,210,133 discloses a vaginal speculum having a microscope mounted thereon which has a light source for illumination and is longitudinally adjustable for focusing.

VanDerBel U.S. Pat. No. 4,597,383 discloses a vaginal speculum having optical fiber illumination means attached thereto.

Burgin U.S. Pat. No. 4,638,792 has an adjustable speculum with an incorporated light system.

Walsh U.S. Pat. No. 4,619,248 discloses a light attachment for a speculum.

Wider et al. U.S. Pat. No. 4,562,832 illustrates in FIG. 6 a fiberoptic light pipe installed in the lower jaw of the vaginal speculum.

Burgin U.S. Pat. No. 4,502,468 has an adjustable speculum with an incorporated lighting system.

Whitman U.S. Pat. No. 3,789,835 discloses an illuminating attachment for vaginal speculum.

Stafl U.S. Pat. No. 4,300,570 has a diagnostic method of projecting the image of a cervix photograph onto a screen. However, the camera is not mounted to the speculum.

Hasson U.S. Pat. No. 3,789,829 discloses a radium applicator mounted to a vaginal speculum.

Walden et al. U.S. Pat. No. 3,037,505 discloses a speculum with a spray tube carried by a jaw of the speculum.

Tanikawa et al. U.S. Pat. No. 4,461,558 discloses an endoscopic photographing apparatus applicable to all types of endoscopes and uses thereof.

Toyota et al. U.S. Pat. No. 4,697,210 discloses an endoscope for observing the interior of a cavity in a human body with the image displayed on a TV screen.

The last two patents are representative of many observation techniques available for use with endoscopes.

None of these devices have served to increase the detection rate of cancer and the early treatment thereof.

DISCLOSURE OF THE INVENTION

A cervical videoscope apparatus is provided which includes a vaginal speculum having a first fixed blade, a second blade mounted for pivotal movement toward and away from the fixed blade and spring means normally urging the second blade toward the fixed blade. The improvement includes a video camera, optics and light bundle, collectively referred to as an electronic video endoscope or video camera unit. The video camera unit is removably mounted on one of the blades for viewing the cervix, means providing light to the cervix, means for focusing the camera on a selected site on the cervix and means for providing a signal from the camera to a video screen for viewing the cervix and identifying lesions thereon. The focusing means may include a track mounted longitudinally along one of the blades and means for adjusting the video camera unit along the track for focusing. The light providing means can include a light carrier on the track for providing light to the cervix. In addition, means is provided for selecting light for illumination of the cervix at any one of a range of light frequencies. This can be broad frequency light, monochromatic light or laser light for illumination. A particularly useful light frequency has been found to be from 200 nm through 1100 nm. A suitable means for stepping sequentially through the frequencies is a monochromator. The monochromator converts light from a light source to a single frequency at an output in the form of a rectangular slit. A light carrier is provided which includes a bundle of optical fibers having a first end in a form of a rectangular collar for receiving the output from the monochromator and a circular collar at the other end for directing a round column of light onto the cervix.

A laser carrier can be provided on the track for directing a laser beam or laser fiber to vaporize lesions on the cervix. Also, a suction tube can be provided on the track to remove smoke created when the lesions are vaporized with the laser.

The invention also provides a method for locating and surgically removing lesions. This method comprises the steps of selectively illuminating the cervix with a light of different frequencies, observing the cervix as it is illuminated with each light frequency, locating lesions by their florescence or reflectance under one of the selected light frequencies and removing the lesions which have been located. The lesions may be removed by using a laser to vaporize them and the activation of the laser can be terminated in response to termination of any florescence at the lesion site.

The video camera unit is removably attached to one blade of the speculum, as by a flexible strap having a first end fixedly attached to the first side of the track and extending around the video camera unit and having a second end with means for releasably attaching it to the second side of the track. This releasable means may include a pin on the second side of the track, an aperture in the second end of the strap having a diameter just slightly larger than the diameter of the pin so as to be received thereover and a removable fastening means attached to the end of the pin to hold the second end in place.

After removal from the speculum, the video camera unit can be inserted in an outer, cylindrical, heat sterilizable sheath having a window sealed to the distal end thereof and an accordian-folded, heat sterilizable, cylindrical sleeve mounted adjacent to the proximate end of the sheath and extendable along the electronic cable and optical bundle of the video camera unit for a substantial distance for maintaining sterility of the video camera unit within an operating room. Also, means can be provided for releasably locking the video camera unit within the sheath in a predetermined orientation. This releasable locking means may be in the form of a bayonet slot and pin arrangement. The sheath may have a passageway or channel within it for supplying an insufflation gas to distend the area being examined, along with valve means for controlling the flow of gas to the channel. A second channel can also be provided with a steerable device or other means for carrying out a procedure on a lesion located at the site.

Afterwards, the video camera unit can be removed from the sheath, resterilized or disinfected and reattached to a sterile speculum for examination of the next patient. The sheath can be thrown away or resterilized for reuse with another patient.

Additional advantages of this invention will become apparent from the description which follows, taken in conjunction with the accompanying drawings.

BRIEF DESCRIPTION OF THE DRAWINGS

FIG. 1 is a side elevation of a cervical videoscope constructed in accordance with this invention and positioned for use;

FIG. 2 is an enlarged rear elevation of the cervical videoscope of FIG. 1;

FIG. 3 is a longitudinal section, taken along line 3—3 of FIG. 2; showing further details of the video camera and associated laser tube and suction tube;

FIG. 4 is a longitudinal section, taken along line 4—4 of FIG. 2, showing details of the track mounting for the video camera unit;

FIG. 5 is an enlarged cross-section, taken along line 5—5 of FIG. 4, showing further details of the video camera unit and track mechanism;

FIG. 6A is a diagrammatical view of video camera unit used in conjunction with a monochromator;

FIG. 6B shows details of the optical bundle connector of FIG. 6A for converting a rectangular light slit into a circular beam;

FIG. 7 is a diagrammatical view showing the video camera unit used with a band pass filter to provide monochromatic light;

FIG. 8 is a diagrammatical view showing the video camera unit used directly with a light source;

FIG. 9 is a fragmentary side elevation of a video camera unit and light source attached to the speculum by a releasable strap;

FIG. 10 is an enlarged vertical section, taken along line 10—10 of FIG. 9, showing further details of the removable strap;

FIG. 11 is a perspective view of the video camera unit and the sheath into which it is to be inserted;

FIG. 12 is a fragmentary perspective view showing the video camera unit inserted within the sheath;

FIG. 13 is an enlarged, end view of the distal end of the sheath of FIG. 12; and FIG. 14 is an enlarged vertical section, taken along line 14—14 of FIG. 12, showing the interconnection between the video camera unit and the sheath.

BEST MODE FOR CARRYING OUT THE INVENTION

In accordance with this invention a cervical videoscope V is attached to a speculum S, as shown in FIG. 1. In use, the speculum is inserted into the vagina as shown. The speculum includes a lower fixed blade 10 having a depending handle portion 12. An upper pivotal blade 14 generally extends parallel to lower blade 10 and has depending ears 16 at the proximate by which it is pivotally mounted on a support 18. Support has a yoke 20 at the upper end thereof to which ears 16 are pivoted. The lower portion of support 18 has a longitudinal slot 22 through which a thumb screw 24 extends for tightening against handle 12 to adjust the spacing of upper blade 14 from lower blade 10.

At the pivotal connection between ears 16 and yoke 20 a spring (not shown) may be provided which tends to pivot the upper blade 14 in a counterclockwise direction, as viewed in FIG. 1, so that it is moved toward fixed blade 10. However, this movement is limited by the position of nut 26 on threaded adjustment rod 28. Conveniently, rod 28 extends through a lever 30 which is fixedly attached to one of the ears 16 of upper pivotal blade 14. Thus, when nut 26 is moved outwardly along rod 28, blade 14 will pivot toward blade 10 and when nut 26 is moved inwardly along rod 28 blade 14 will pivot away from blade 10.

The videoscope V includes a video camera unit 32 mounted on lower blade 10. As previously explained, the video camera unit includes the camera, optics and light delivery system and may also be referred to as an electronic video endoscope. A longitudinal guide member 34 is fixedly attached to stationary blade 10, as best seen in FIG. 4. Worm gear 36 is mounted within guide 34, as shown, for rotation about a pin 38. Video camera unit 32 is provided with a rack 40 extending longitudinally therealong and attached thereto. The teeth of the rack engage worm gear 36. A control shaft 42 is attached to pin 38 and has a knob 44 for rotating worm gear 36 and thereby adjusting video camera unit 32 longitudinally along guide 34. This provides a means for focusing the video camera unit on the particular area of the cervix which is being investigated. Advantageously, the video camera unit is sealed against moisture leakage into the electronics to allow soaking in a sterilizing or disinfecting solution between usage on different patients. It is usually backfilled with nitrogen during manufacture after air and moisture is removed in a vacuum chamber. A CCD sensor can be used to pickup the image and transmit a signal to the video monitor for processing. The video camera unit case can be made of titanium-or other metal which is substantially non-corrosive or it can be made of plastic. The video camera unit can also be sterilized with a gas, such as ethylene oxide.

At the forward end of video camera unit 32 is an optical lens system 46 for receiving an image from the cervix. This lens system may have zoom capabilities to provide 2× to 200× magnification. The image is projected by the camera along cable 48 to a video control unit 50 for projecting an image onto monitor 51 shown in FIG. 6A. As shown in FIG. 6A, a light source, such as xeon light source, 52 projects light through a monochromator 54. Other light sources, such as halogen, mercury vapor, mercury arc, incandescent or laser can be used. The monochromator has the ability to project light of a single wavelength from the light source 52 and to do so in stepped increments. It should have a high output with a frequency range from 200 nm to 1100 nm. By this means, a physician can look at the video monitor while stepping through each light frequency and look for fluorescing lesions on the cervix or in the vagina. It has been found that different types of lesions will fluoresce in response to different light wavelengths.

The light exits the monochromator 54 through a slit 56 shown in FIG. 6B and enters one end of a bundle of optical fibers 58. Conveniently, one end of optical fiber bundle 58 is mounted within a rectangular collar 60 which mates with the end of monochromator 54 for receiving light from slit 56. The other end of optical fiber bundle 58 has a circular collar 62. Collar 62 and the cable 48 for video control unit 50 connect to a cable or light carrier 64 wherein the individual optical fibers 64 are positioned around the outside of the lens system 46, as best seen in FIG. 5. Thus, the light image of selected wavelength can be directed substantially uniformly onto the surface of the cervix or vagina. As the monochromator steps the light from one end of the light spectrum to the other, a wavelength will be encountered in which cancerous lesions or lesions caused by viral infection will fluoresce and therefore will be identifiable on the video monitor. The florescence of the tissue may be natural fluorescence, or it may be fluorescence produced by substances which selectively enter cancer cells such as hematoporphyrin derivative (HPD).

When this occurs, these lesions can be destroyed by use of a laser beam. This is accomplished by directing the laser bean along an optical fiber 66 which extends through a channel 68 attached to guide member 34. Optical fiber 66 can be provided with steering cables (not shown) for directing the laser to the lesion cite. A KPT-532 laser, carbon dioxide laser or a YAG laser having been found to be satisfactory. Conveniently, a suction channel 70 can be provided adjacent to laser channel 68 for removing smoke caused by destruction of the lesions. This channel may be connected to a vacuum hose 72, as shown in FIG. 3.

An alternative arrangement is shown in FIG. 7 wherein a removable band pass filter 74 is provided between the light source 52 and optical fiber bundle 58 for providing selected wavelengths of light to the cervix. A band pass filter is useful when the patient is treated with a substance which will accumulate at the lesion cite and be fluorescent under a known wavelength of light. In such a case the band pass filter can be selected to transmit only the desired wavelength frequency. Suitable substances are hematoporphyrin (HPD) or a derivative thereof, such as dehematoporphyrin either (DHE), corins, pheophorbides and coumerins. Also Rhodamine-123 can be sprayed or painted on the cervix. Finally, the site can be tagged with a fluorescent tagged monoclonal antibody.

In a still further simplified embodiment, shown in FIG. 8, the light source 52 is directly connected to optical fiber bundle 58. This embodiment can be used wherein the material at the lesion site on the cervix will have florescence over a wide range of light wavelengths for identification of lesions.

A number of add-ons may be provided to the apparatus just described. Among these are a character generator for the patient's name, age, etc., video recorder, video printer and suitable image processors.

A further alternative embodiment is shown in FIGS. 9 and 10 wherein a videoscope V' is removably attached to blade 10 of speculum S by means of a flexible strap So fixedly attached to one side of rack 40 and extending around the camera unit body and being attached to the other side of rack 40. This attachment may comprise a threaded stud 82 which receives an aperture 84 in the free end of strap 80. This end of strap 80 is held in place by means of a removable nut 86.

With this arrangement, the videoscope V' can be used on the speculum S in the manner previously described. However, the blades of the speculum cover much of the surface of the vagina which prevent thorough inspection thereof. Thus, by removing the videoscope from the speculum the scope can then be reinserted into the vagina, as described more fully below so that the areas which were not visible because of the speculum blades can now be examined.

Conveniently, for use without the speculum, the camera can be inserted into a sterile sheath H, as best seen in FIGS. 11–14. This sheath H is substantially similar to that shown in my U.S. Pat. No. 4,878,485 for "Rigid Video Endoscope With Heat Sterilizable Sheath" which issued on Nov. 7, 1989. The sheath includes a cylindrical housing 88 having a window 90 at the distal end thereof and an accordian-folded sleeve 92 at the proximate end thereof. The housing 88 may be provided with one or more channels, such as channel 94 which can provide gas under pressure by means of a valve 96 and extends longitudinally through housing 88 and below window 90, as shown. Similarly, a second channel 98 can be provided through which a steerable device 100 is provided.

When the videoscope V' is inserted within sheath H, it can be held in fixed position by means of oppositely projecting pins 102 at the proximate end thereof which engage a bayonet slot 104 in an internal sleeve 106 within housing 88, as best seen in FIGS. 12 and 14. After insertion, sleeve 92 can be pulled longitudinally down cable 48 by means of pull ring 108. Then the sheath and camera can be inserted into the vagina to examine portions which were previously covered with the speculum. Also, this apparatus can be used for inspection of bodily surfaces or in the colon and other areas where lesions might be suspected. Conveniently, a passageway 110 is provided along the exterior of housing 88 through which channels 94 and 98 can extend, as best seen in FIG. 14.

Afterwards, the camera unit can be removed from the sheath, resterilized and reattached to a sterile speculum for examination of the next patient. The sheath can be thrown away or resterilized or disinfected and reattached to a sterile speculum for reuse with another patient.

From the foregoing, the advantages of this invention are readily apparent. A simple yet highly useful cervical videoscope has been provided which can easily be used by the doctor to exam the cervix and vagina for cancerous lesions or other abnormalities. Also, because of the small size of the camera unit there is sufficient space between the camera unit and the blades of the speculum for inserting forceps and other instruments that may need to be used. By using the cervical videoscope in combination with a monochromator the physician can step the wavelength of light from one end of the light spectrum to the other until he observes florescence which identifies abnormal cells. Thereupon, he can destroy the cells by use of a laser beam. When he observes that no more florescence is occurring, then he can discontinue the operation of the laser, knowing that the lesion has been completely eradicated. Also, a channel for drawing a suction to remove smoke created by the destruction of the lesion can be provided. Finally, the camera is adjustable along a guide on the fixed blade of the speculum to focus it.

It should also be noted that the device may be detached from the vaginal speculum and used along with the sophisticated light sources to look for similar lesions in the rectal area or on other body surfaces. Conveniently, the camera unit, after removal from the speculum, can be inserted into a sterile sheath in fixed relation therewith. This combined unit can then be inserted into the vagina to examine areas which were previously covered by the blades of the speculum. It also can be used for examining the colon and other areas where lesions are suspected.

This invention has been described in detail with reference to particular embodiments thereof, but it will be understood that various other modifications can be effected within the spirit and scope of this invention.

I claim:

1. A method of examining various internal body surfaces for lesions having predetermined characteristics, said method comprising the steps of:

mounting a video camera unit and a source of illumination on a blade of a vaginal speculum, wherein the video camera unit has a cable trailing from the distal end thereof and the light source has an optical bundle trailing from the distal end thereof;

inserting the speculum into the vagina of the patient;

illuminating the cervix and inspecting it for lesions;

removing the speculum from the vagina and removing the video camera unit and illumination source from the speculum;

inserting the video camera unit and illumination source into a cylindrical, sterilizable sheath, having a window at a distal end and an accordian-folded cylindrical sleeve adjacent the proximate end;

pulling the sleeve over the trailing cable and optical bundle;

inserting the sheath, with the video camera unit and light source in place into one or more body passageways to position the video camera unit for viewing a selected site; and examining the site for lesions.

2. A method, as claimed in claim 1, including the further steps of:

removing the sheath from the passageway;

removing the sheath from the video camera unit and light source;

sterilizing or disinfecting the video camera unit and light source; and attaching the video camera unit and light source to the blade of a sterile speculum for examining another patient.

3. A method, as claimed in claim 1, including the further steps of:

removing any lesions found.

4. A method, as claimed in claim 1, including the further step of:

supplying insufflation gas through a channel in the sheath to distend the area being examined.

* * * * *